United States Patent [19]

Sugiura et al.

[11] Patent Number: 5,296,238
[45] Date of Patent: Mar. 22, 1994

[54] MICROBICIDES

[75] Inventors: Koji Sugiura; Satoru Maekawa, both of Nagoya; Hidemu Inoue, Seto; Takuya Oomura, Tokyo; Hideki Kato; Hiroki Kourai, both of Tokushima, all of Japan

[73] Assignee: Toagosei Chemical Industry Co., Inc., Tokyo, Japan

[21] Appl. No.: 659,960

[22] Filed: Feb. 26, 1991

[51] Int. Cl.$^5$ .................. A01N 59/16; A01N 59/26
[52] U.S. Cl. ................... 424/604; 424/606; 424/601; 424/617; 424/618; 423/306; 423/311; 423/312
[58] Field of Search ............... 424/604, 606, 617, 618; 423/306, 311; 210/688, 764

[56] References Cited

U.S. PATENT DOCUMENTS

| | | | |
|---|---|---|---|
| 1,170,056 | 2/1916 | Engelmann | 424/604 |
| 4,025,608 | 5/1977 | Tawil et al. | 423/311 |
| 4,059,679 | 11/1977 | Clearfield | 423/306 |
| 4,906,464 | 3/1990 | Yamamoto et al. | 424/489 |
| 4,938,955 | 7/1990 | Niira et al. | 424/78.1 |
| 4,938,958 | 7/1990 | Niira et al. | 424/78.1 |

FOREIGN PATENT DOCUMENTS

| | | | |
|---|---|---|---|
| 58-077805 | 5/1983 | Japan | 424/617 |
| 62-083309 | 4/1987 | Japan | 423/306 |
| 265809 | 11/1988 | Japan . | |
| 0296508 | 4/1990 | Japan . | |
| 662491 | 5/1979 | U.S.S.R. | 423/306 |
| 2224727 | 6/1990 | United Kingdom . | |

OTHER PUBLICATIONS

James Alamo et al., UltraLow-Expansion Ceramics in the System Na$_2$O-ZrO$_2$-P$_2$O$_5$-SiO$_2$, Communications of the American Ceramic Society, May 1984.

Lars-Ove Hagman et al., The Crystal Structure of NaMe$_2^{IV}$(PO$_4$)$_3$; Me$^{IV}$=Ge, Ti, Zr, Acta Chemica Scandinavica, 22, pp. 1822-1832, (1968).

Sridhar Komarneni, Hydrothermal Preparation of the Low-Expansion NZP Family of Materials, International Journal High Technology Ceramics, 4, pp. 31-39, (1988).

Katsuhiko Itoh et al., Synthesis of Properties of Crystalline Zirconium Phosphates, Advances in Ceramics, vol. 24: Science and Technology of Zirconia III, 1988, pp. 1007-1014.

Clearfield, A. et al. "Synthesis of Sodium Dizorconium . . . " Mat. Res. Bull., vol. 15 (11), Nov. 1980, pp. 1603-1610.

Chemical Abstracts 113: 206704t, abstracting JP 02 96508, published Apr. 9, 1990.

Primary Examiner—Allen J. Robinson
Assistant Examiner—John D. Pak
Attorney, Agent, or Firm—Browdy and Neimark

[57] ABSTRACT

The present invention provides a microbicide which comprises a phosphate represented by the following general formula:

$$M_a^1 A_b M_c^2 (PO_4)_d \cdot nH_2O$$

wherein M$^1$ represents at least one element selected from the group consisting of silver, copper, zinc, tin, mercury, lead, iron, cobalt, nickel, manganese, arsenic, antimony, bismuth, barium, cadmium and chromium, M$^2$ represents at least one element selected from tetravelent metal elements, A represents at least one ion selected from the group consisting of hydrogen ion, alkali metal ions, alkaline earth metal ions and ammonium ion, n represents a number which satisfies $0 \leq n \leq 6$, a and b each represents a positive number and satisfy la+mb=1 or la+mb=2, and when a and b satisfy la+mb=1, c is 2 and d is 3, and when a and b satisfy la+mb=2, c is 1 and d is 2, where l is valence of M$^1$ and m is valence of A.

8 Claims, No Drawings

MICROBICIDES

The present invention relates to a microbicide which contains, as an active ingredient, a specific phosphate containing a metal ion having antibacterial, antifungal or antialgal activity such as silver, copper, zinc, tin, mercury, lead, iron, cobalt, nickel, manganese, arsenic, antimony, bismuth, barium, cadmium or chromium ion, and the microbicide can be used as antimicrobial compositions which comprise the microbicide mixed with various binders or as antimicrobial shaped products which comprise the microbicide supported on carriers such as fibers, films, papers, and plastics.

Silver, copper, zinc, tin, mercury, lead, iron, cobalt, nickel, manganese, arsenic, antimony, bismuth, barium, candmium and chromium have been known for a long time as metals which exhibit antifungal, antialgal and antibacterial activities (hereinafter referred to as "antimicrobial metals"), and particularly silver has been widely used in the form of aqueous silver nitrate solution as bactericides or disinfectants. However, the above-mentioned metal ions exhibiting antifungal, antialgal and antibacterial activities are, in many cases, toxic for human bodies and have various limitations in methods of use, storage and disposal, and thus their use is limited.

Recently, it has become clear that application of a slight amount of antimicrobial metal to subjects is enough to exhibit antifungal, antialgal and antibacterial activities, and various inorganic microbicides having antifungal, antialgal and antibacterial activities which comprise antimicrobial metals supported on inorganic ion exchangers or porous materials have been proposed.

As compared with organic microbicides, inorganic microbicides have the characteristics that they are higher in safety, have prolonged antimicrobial effect, and besides are superior in heat resistance.

As one of them, there is a microbicide prepared by replacing the metal ion in clay minerals such as zeolite with silver ion, but since acid resistance of skeleton structure of the clay mineral per se is low, silver ion readily flows away in acidic solution and it has no durable antimicrobial effect. Besides, silver ion is unstable against exposure to heat and light and is immediately reduced to metallic silver to cause coloration and thus, this microbicide has problem in long-term stability. In order to increase stability of silver ion, an attempt has been made to support both silver and ammonia on zeolite by ion exchanging, but the problem of coloration has not yet been solved to practically available level and fundamental solution has not been made.

Furthermore, there is another microbicide which comprises an antimicrobial metal supported on an active carbon having adsorbability. However, since a soluble antimicrobial metal is merely physically adsorbed or deposited, when the microbicide is allowed to contact with water, the antimicrobial metal ion is rapidly dissolved away and it is difficult to retain the antimicrobial effect for a prolonged period of time.

The object of the present invention is to provide a material which exhibits maximum antifungal, antialgal and antibacterial activities of silver, copper, zinc, tin, mercury, lead, iron, cobalt, nickel, manganese, arsenic, antimony, bismuth, barium, cadmium and chromium ions. That is, the object of the present invention is to provide a material which does not undergo coloration and furthermore, exhibits antifungal, antialgal and antibacterial activities for a prolonged period of time even under severe conditions by chemically and physically stably keeping antimicrobial metal ions.

As a result of intensive research conducted by the inventors in an attempt to attain the above object, it has been found that specific phosphates having metal ions which have antimicrobial activity such as silver, copper, zinc, tin, mercury, lead, iron, cobalt, nickel, manganese, arsenic, antimony, bismuth, barium, cadmium and chromium ions, especially silver ion, have markedly excellent chemical and physical stability and besides, can exhibit antifungal, antialgal and antibacterial activities for a long period of time. Thus, the present invention has been accomplished.

That is, the present invention relates to a microbicide comprising a phosphate represented by the following general formula:

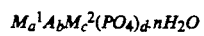

$$M_a{}^1 A_b M_c{}^2 (PO_4)_d \cdot nH_2O$$

wherein $M^1$ represents at least one element selected from silver, copper, zinc, tin, mercury, lead, iron, cobalt, nickel, manganese, arsenic, antimony, bismuth, barium, cadmium and chromium, $M^2$ represents at least one element selected from tetravalent metal elements, A represents at least one ion selected from hydrogen ion, alkali metal ion, alkaline earth metal ion, and ammonium ion, n is a number which satifies $0 \leq n \leq 6$, a and b are positive numbers and satisfy $la + mb = 1$ or $la + mb = 2$, and when a and b satisfy $la + mb = 1$, c is 2 and d is 3, and when a and b satisfy $la + mb = 2$, c is 1 and d is 2 where 1 is valence of $M^1$ and m is valence of A.

The compounds used in the present invention and method of use thereof will be explained.

The compounds used in the present invention are phosphates represented by the following general formula:

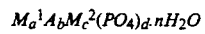

$$M_a{}^1 A_b M_c{}^2 (PO_4)_d \cdot nH_2O$$

wherein $M^1$ represents at least one element selected from silver, copper, zinc, tin, mercury, lead, iron, cobalt, nickel, manganese, arsenic, antimony, bismuth, barium, cadmium, and chromium, $M^2$ represents at least one element selected from tetravalent metal elements, A represents at least one ion selected from hydrogen ion, alkali metal ion, alkaline earth metal ion, and ammonium ion, n is a number which satisfies $0 \leq n \leq 6$, a and b are positive numbers and satisfy $la + mb = 1$ or $la + mb = 2$, and when a and b satisfy $la + mb = 1$, c is 2 and d is 3, and when a and b satisfy $la + mb = 2$, c is 1 and d is 2, where 1 represents valence of $M^1$ and m represents valence of A.

The phosphate represented by the above general formula where a and b satisfy $la + mb = 1$ and c is 2 and d is 3, is a compound having amorphous or network structure, and the phosphate represented by the above general formula where a and b satisfy $la + mb = 2$ and c is 1 and d is 2, is a compound having amorphous or layer structure. The phosphate having network structure is preferred in the present invention.

Silver, copper, zinc, tin, mercury, lead, iron, cobalt, nickel, manganese, arsenic, antimony, bismuth, barium, cadmium and chromium show antifungal, antialgal and antibacterial effects and furthermore, copper, zinc, tin, lead, nickel, manganese, bismuth, cadmium and chromium contribute also to stabilization of the phosphates.

In the present invention, silver is especially preferred from the points of stability and antimicrobial activity.

The alkali metal ion includes, for example, lithium, sodium and potassium ions, and the alkaline earth metal ion includes, for example, magnesium and calcium ions, and lithium, sodium, potassium and magnesium ions are preferred for the present invention in consideration of stability of the resulting compounds and cheapness of them.

The tetravelent metals include, for example, zirconium, titanium and tin, and zirconium and titanium are preferred in the present invention from the point of safety.

Typical examples of the phosphates are as follows:

$Ag_{0.005}Li_{0.995}Zr_2(PO_4)_3$ $Ag_{0.01}(NH_4)_{0.99}Zr_2(PO_4)_3$ $Ag_{0.05}Na_{0.95}Zr_2(PO_4)_3$ $Ag_{0.20}K_{0.80}Ti_2(PO_4)_3$ $Ag_{0.01}H_{0.95}Li_{0.04}Zr_2(PO_4)_3$ $Ag_{0.05}H_{0.85}Li_{0.10}Zr_2(PO_4)_3$ $Ag_{0.10}H_{0.80}Li_{0.10}Ti_2(PO_4)_3$ $Ag_{0.10}H_{0.85}Li_{0.05}Zr_2(PO_4)_3$ $Ag_{0.20}H_{0.75}Na_{0.05}Ti_2(PO_4)_3$ $Ag_{0.30}H_{0.45}Na_{0.25}Zr_2(PO_4)_3$ $Ag_{0.35}H_{0.60}Na_{0.05}Sn_2(PO_4)_3$ $Ag_{0.50}H_{0.45}K_{0.05}Sn_2(PO_4)_3$ $Ag_{0.50}H_{0.40}Li_{0.10}Ti_2(PO_4)_3$ $Ag_{0.70}H_{0.25}K_{0.05}Ti_2(PO_4)_3$ $Ag_{0.92}H_{0.05}Li_{0.03}Zr_2(PO_4)_3$ $Ag_{0.001}Li_{1.999}Zr_2(PO_4)_2$ $Ag_{0.01}Na_{1.99}Zr_2(PO_4)_2$ $Ag_{0.01}K_{1.99}Sn(PO_4)_2 \cdot 1.2H_2O$ $Ag_{0.1}(NH_4)_{1.9}Ti(PO_4)_2 \cdot 4H_2O$ $Ag_{0.005}H_{1.995}Zr(PO_4)_2 \cdot H_2O$ $Ag_{0.50}H_{1.50}Zr(PO_4)_2 \cdot H_2O$ Examples of the compounds having the above formulas in which a part or the whole of Ag is replaced with Zn, Mn, Ni, Pb, Hg, Sn, Cr, Bi or Cu are as follows:

$Cu_{0.200}Na_{0.040}H_{1.56}Zr(PO_4)_2 \cdot 2H_2O$ $Cu_{0.010}H_{1.980}Zr(PO_4)_2 \cdot H_2O$ $Cr_{0.010}H_{1.70}Zr(PO_4)_2 \cdot H_2O$ $Bi_{0.010}H_{1.70}Zr(PO_4)_2 \cdot H_2O$ $Cr_{0.200}Na_{0.300}H_{1.100}Zr(PO_4)_2 \cdot 3H_2O$ $Bi_{0.200}Na_{0.300}H_{1.100}Zr(PO_4)_2 \cdot 3H_2O$ For preparing these phosphates there are firing method, wet method, hydrothermal method and the like, and specifically, for example, the following can be referred to. The phosphates of the present invention can be easily obtained by these methods.

That is, an oxychloride having a tetravalent metal such as zirconium, titanium or tin as a constituent element, for example, zirconium oxychloride, titanium oxychloride or tin oxychloride is added to a concentrated aqueous phosphoric acid solution, and after refluxing under heating for 24 hours, the precipitate is subjected to filtration, washing with water, drying and grinding to obtain a phosphate such as zirconium phosphate [$Zr(HPO_4)_2 \cdot H_2O$]. This phosphate is immersed in an aqueous solution which contains an antimicrobial metal at a suitable concentration, thereby to obtain the phsophate of the present invention.

When ions such as $Cu^{2+}$, $Zn^{2+}$, $Sn^{2+}$, $Mn^{2+}$, $Hg^{2+}$, $Bi^{2+}$, $Cd^{2+}$ and $Cr^{2+}$ are selected as the antimicrobial metal, it is necessary to immerse the above phosphate such as zirconium phosphate [$Zr(HPO_4)_2 \cdot H_2O$] in an aqueous solution containing an alkali metal or alkaline earth metal before it is immersed in the aqueous solution containing the antimicrobial metal.

Furthermore, phosphates of network structure such as zirconium phosphate are prepared in the following manner.

Oxalic acid is added to an aqueous solution of zirconium oxynitrate and sodium nitrate with stirring and phosphoric acid is further added thereto. This is adjusted to a pH of 3.5 with aqueous sodium hydroxide solution and is refluxed under heating for 78 hours and the precipitate is subjected to filtration, washing with water, drying and grinding to obtain zirconium phosphate [$NaZr_2(PO_4)_3$] of network structure. This zirconium phosphate is immersed in an aqueous solution containing an antimicrobial metal at a suitable concentration to obtain the phosphate of the present invention which has network structure.

Another method is as follows. A compound containing an alkali metal such as lithium carbonate ($Li_2CO_3$) or sodium carbonate ($Na_2CO_3$), a compound containing zirconium, titanium or tin such as zirconium oxide $ZrO_2$ or titanium oxide $TiO_2$, and a compound containing a phosphate group such as ammonium dihydrogenphosphate $NH_4H_2PO_4$ are mixed at a molar ratio of about 1:4:6, and this mixture is fired at 1000–1400° C. to obtain a phosphate. This is immersed in an aqueous solution of an inorganic acid such as nitric acid, sulfuric acid or hydrochloric acid at room temperature-100° C. to obtain a raw material phosphate [$H_{(l-x)}A_xM_2^2(PO_4)_3$]. The resulting raw material phosphate is immersed in an aqueous solution containing silver ion at a suitable concentration to obtain the phosphate of the present invention.

The phosphates of the present invention with a larger value of a have tendency to exhibit the higher antifungal, antialgal and antibacterial activities more strongly, but even when the value of a is very small, antifungal, antialgal and antibacterial activities can be exhibited. However, when the value of a is less than 0.001, it may become difficult to exhibit antifungal, antialgal and antibacterial activities for a prolonged period of time, and furthermore in consideration of cost for the antimicrobial metals used, the value of a is preferably at least 0.001, more preferably 0.01–0.5.

Furthermore, the value of a can be suitably adjusted depending on the desired characteristics and conditions of use and can be suitably changed by adjusting concentration of an antimicrobial metal in the aqueous solution or time or temperature for immersing the raw material phosphate in the aqueous solution.

The phosphates used in the present invention are stable against exposure to heat and light, and neither structure nor composition of the phosphates changes even after heated at 500° C. and at 800° C. for some ones and besides, they undergo no change in color even by irradiation with ultraviolet ray. Furthermore, no change is seen in skeleton structure even in acidic solution. Therefore, the phosphates of the present invention are not restricted by conditions such as heating temperature and light-proof conditions when they are processed for obtaining molded products, are stored and are used, while the conventional microbicides have been restricted by them.

Form of the microbicide of the present invention in use has no special limitation, and the microbicide can be suitably mixed with other components or formed into a composite with other materials depending on uses. For example, the microbicide of the present invention can be used in various forms such as powder, powder-containing dispersion, powder-containing particles, powder-containing paint, powder-containing fiber, powder-containing paper, powder-containing filter, powder-containing film and powder-containing aerosol. Furthermore, if necessary, it can be used in combination with various additives or materials used for deodorizers, flameproofing agents, corrosion proofing agents, fertilizers, and building materials.

The microbicides of the present invention exhibit antifungal, antialgal and antibacterial activities for any use against fungi, algae and bacteria on which antimicrobial metal ions such as silver ion effectively act, and can be effectively used, for example, for the following uses: fibers such as working clothes, medical clothes, medical bedclothes, sports wears, medical dressings, fishing nets, curtains, carpets, underwears, and air filters; papers such as wall papers; films such as food-packaging films, medical films, and synthetic leather; paints such as paints for sterilizers, corrosion-resistant paints, and antifungal paints; powders such as agricultural soil; and liquid compositions such as shampoo.

The present invention will be explained in detail by the following referential examples, examples and comparative examples.

First, the following three kinds of phosphates as raw materials were prepared.

REFERENTIAL EXAMPLE 1

Zirconium oxychloride was added to a concentrated aqueous phosphoric acid solution. This was refluxed under heating for 24 hours and then, the precipitate was subjected to filtration, washing with water, drying and grinding to obtain zirconium phosphate $Zr(HPO_4)_2 \cdot H_2O$.

REFERENTIAL EXAMPLE 2

Titanium phosphate $Ti(HPO_4)_2 \cdot H_2O$ was obtained in the same manner as in Referential Example 1 except that titanium tetrachloride was used in place of Zirconium oxychloride.

REFERENTIAL EXAMPLE 3

Tin phosphate $Sn(HPO_4)_2 \cdot H_2O$ was obtained in the same manner as in Referential Example 1 except that tin chloride was used in place of zirconium oxychloride.

EXAMPLE 1

Microbicides were prepared by the following method using powders of the phosphates obtained in Referential Examples 1–3.

That is, 8 kinds of aqueous solutions containing a nitrate of antimicrobial metal at various concentrations were prepared (acidified with nitric acid in the case of bismuth). The powders obtained in Referential Examples 1–3 were added to these aqueous solutions and stirred for various periods of stirring time. Then, the resulting slurries were filtrated and the residue was washed with pure water until antimicrobial metal ion was no longer detected in the washing liquid according to atomic absorption spectrometry.

Separately, some of the powders obtained in Referential Examples 1–3 were added to aqueous solutions of nitrates of sodium, magnesium and ammonium before added to the aqueous solutions of nitrates of antimicrobial metals, and were subjected to stirring, washing with water, drying and grinding and thereafter were subjected to the same procedures as above.

Then, the residue thus washed was subjected to wet grinding using water as a medium and then, to classification using a screen to finally collect fine particles of 1.0 μm or less. Furthermore, the fine particles were dried by heating at 110° C. overnight to obtain the desired phosphates.

Content of the antimicrobial metal ion in the phosphates thus obtained was calculated by analyzing the concentrations of the antimicrobial metal ion in the filtrate and in the aqueous solution of nitrate of antimicrobial metal before contacted with the powders obtained in Referential Examples 1–3.

The phosphates obtained in the above method are shown in Table 1. These phosphates had excellent performances as microbicides as shown in the results of the following evaluations.

TABLE 1

| Sample No. | Microbicides |
| --- | --- |
| 1 | $Ag_{0.200}H_{1.800}Zr(PO_4)_2 \cdot H_2O$ |
| 2 | $Cu_{0.005}H_{1.990}Zr(PO_4)_2 \cdot H_2O$ |
| 3 | $Cu_{0.400}Na_{0.040}H_{1.160}Zr(PO_4)_2 \cdot 2H_2O$ |
| 4 | $Zn_{0.400}Na_{0.040}H_{1.160}Zr(PO_4)_2 \cdot 2H_2O$ |
| 5 | $Mn_{0.400}Na_{0.040}H_{1.160}Zr(PO_4)_2 \cdot 2H_2O$ |
| 6 | $Pb_{0.010}H_{1.980}Zr(PO_4)_2 \cdot H_2O$ |
| 7 | $Hg_{0.010}H_{1.980}Zr(PO_4)_2 \cdot H_2O$ |
| 8 | $Sn_{0.400}Na_{0.040}H_{1.160}Zr(PO_4)_2 \cdot 2H_2O$ |
| 9 | $Cd_{0.010}H_{1.980}Zr(PO_4)_2 \cdot H_2O$ |
| 10 | $Bi_{0.005}H_{1.985}Zr(PO_4)_2 \cdot H_2O$ |
| 11 | $Cr_{0.200}Na_{0.300}H_{1.100}Zr(PO_4)_2 \cdot 3H_2O$ |
| 12 | $Ag_{0.200}H_{1.800}Ti(PO_4)_2 \cdot H_2O$ |
| 13 | $Cu_{0.005}H_{1.990}Ti(PO_4)_2 \cdot H_2O$ |
| 14 | $Cu_{0.400}Na_{0.040}H_{1.160}Ti(PO_4)_2 \cdot 2H_2O$ |
| 15 | $Zn_{0.400}Na_{0.040}H_{1.160}Ti(PO_4)_2 \cdot 2H_2O$ |
| 16 | $Mn_{0.400}Na_{0.040}H_{1.160}Ti(PO_4)_2 \cdot 2H_2O$ |
| 17 | $Pb_{0.010}H_{1.980}Ti(PO_4)_2 \cdot H_2O$ |
| 18 | $Hg_{0.010}H_{1.980}Ti(PO_4)_2 \cdot H_2O$ |
| 19 | $Sn_{0.400}Na_{0.040}H_{1.160}Ti(PO_4)_2 \cdot 2H_2O$ |
| 20 | $Cd_{0.010}H_{1.980}Ti(PO_4)_2 \cdot H_2O$ |
| 21 | $Bi_{0.005}H_{1.985}Ti(PO_4)_2 \cdot H_2O$ |
| 22 | $Cr_{0.200}Na_{0.300}H_{1.100}Ti(PO_4)_2 \cdot 3H_2O$ |
| 23 | $Ag_{0.200}H_{1.800}Sn(PO_4)_2 \cdot H_2O$ |
| 24 | $Cu_{0.005}H_{1.990}Sn(PO_4)_2 \cdot H_2O$ |
| 25 | $Cu_{0.400}Na_{0.040}H_{1.160}Sn(PO_4)_2 \cdot 2H_2O$ |
| 26 | $Zn_{0.400}Na_{0.040}H_{1.160}Sn(PO_4)_2 \cdot 2H_2O$ |
| 27 | $Mn_{0.400}Na_{0.040}H_{1.160}Sn(PO_4)_2 \cdot 2H_2O$ |

TABLE 1-continued

| Sample No. | Microbicides |
|---|---|
| 28 | $Pb_{0.010}H_{1.980}Sn(PO_4)_2 \cdot H_2O$ |
| 29 | $Hg_{0.010}H_{1.980}Sn(PO_4)_2 \cdot H_2O$ |
| 30 | $Cd_{0.010}H_{1.980}Sn(PO_4)_2 \cdot H_2O$ |
| 31 | $Bi_{0.005}H_{1.985}Sn(PO_4)_2 \cdot H_2O$ |
| 32 | $Cr_{0.200}Na_{0.300}H_{1.100}Sn(PO_4)_2 \cdot 3H_2O$ |
| 33 | $Cu_{0.400}Mg_{0.050}H_{1.100}Zr(PO_4)_2 \cdot 2H_2O$ |
| 34 | $Zn_{0.400}(NH_4)_{0.040}H_{1.160}Ti(PO_4)_2 \cdot 2H_2O$ |

Method of evaluation of antimicrobial activity

Evaluation of antimicrobial activity of the microbicides obtained in the above-mentioned manner was conducted by the following method.

That is, each of these microbicides was incorporated into a resin and a resin composition mentioned hereinafter and molded into a disc specimen of 20 mm in diameter or molded into yarns, from which a cloth specimen was made.

The following were used as microorganisms to be tested. That is, *Escherichia coli*, *Pseudomonas aeruginosa*, *Staphylococcus aureus* and *Bacillus subtilis* were used as bacteria, *Candida yeast* and *Saccharomyces yeast* were used as yeasts, and *Aspergillus niger*, Gliocladium, Aureobasidium, and Cladosporium were used as fungi.

As media, Muller-Hinton medium was used for bacteria, and Sabouraud's medium was used for yeasts and fungi.

The above microorganisms to be tested were floated in physiological salline solution at $10^8$/ml, and 0.1 ml of it was dispersed on the above medium by Conradi stick. Judgement of antimicrobial activity was conducted in the following manner. The specimen disc was put thereon, and after cultivation by keeping it for 18 hours at 37° C. for bactria and after cultivation by keeping it for one week at 30° C. for yeasts and fungi, whether inhibition zone was formed or not was observed. When inhibition zone was formed, the sample was judged to have antimicrobial activity.

Evaluation test 1

Each of Sample Nos. 1–34 was added in an amount of 2 parts by weight ("part by weight" will be hereinafter referred to merely as "part") to 100 parts of polyethylene terephthalate dry chips having an intrinsic viscosity [$\eta$] of 0.640 measured in a mixed solvent of phenol/ethane tetrachloride (6:4), and the mixture was melt mixed and injection molded at 270° C. to make a molded product of 20 mm in diameter and 3 mm in thickness. These molded products were evaluated on their antimicrobial activity according to the above-mentioned method of evaluation of antimicrobial activity. The results are shown in Table 2 and Table 3.

Separately, molded products made in the same manner as above using zirconium phosphate, titanium phosphate and tin phosphate prepared in Referential Examples 1–3 and those which were made without adding these phosphates, were also evaluated on their antimicrobial activity to find that inhibition zone was not formed in any of these cases.

From the above results, it can be seen that the molded products containing the microbicide of the present invention have excellent antimicrobial activity.

TABLE 2

| Kind of Microorganisms to be tested | Sample No. | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| *Escherichia coli* | + | + | + | + | + | + | + | + | + | + | + | + | + | + | + | + | + |
| *Pseudomonas aeruginosa* | + | + | + | + | − | + | + | + | + | + | + | + | + | + | + | − | + |
| *Staphylococcus aureus* | + | + | + | + | + | + | + | + | + | + | + | + | + | + | + | + | + |
| *Bacillus subtilis* | + | + | + | + | − | + | + | + | + | + | + | + | + | + | + | − | + |
| Candida yeast | + | + | + | + | + | + | + | + | + | + | + | + | + | + | + | + | + |
| Saccharomyces yeast | + | + | + | + | − | + | + | + | + | + | + | + | + | + | + | − | + |
| Aspergillus niger | + | + | + | + | + | + | + | + | + | + | + | + | + | + | + | + | + |
| Gliocladium | + | + | + | + | − | + | + | + | + | + | + | + | + | + | + | − | + |
| Aureobasidium | + | + | + | + | + | + | + | + | + | + | + | + | + | + | + | + | + |
| Cladosporium | + | + | + | + | − | + | + | + | + | + | + | + | + | + | + | − | + |

Notes:
+Inhibition zone was formed.
−Inhibition zone was not formed.

TABLE 3

| Kind of tested microorganisms | Sample No. | | | | | | | | | | | | | | | | |
|---|---|---|---|---|---|---|---|---|---|---|---|---|---|---|---|---|---|
| | 18 | 19 | 20 | 21 | 22 | 23 | 24 | 25 | 26 | 27 | 28 | 29 | 30 | 31 | 32 | 33 | 34 |
| *Escherichia coli* | + | + | + | + | + | + | + | + | + | + | + | + | + | + | + | + | + |
| *Pseudomonas aeruginosa* | + | + | + | + | + | + | + | + | + | − | + | + | + | + | + | + | + |
| *Staphylococcus aureus* | + | + | + | + | + | + | + | + | + | + | + | + | + | + | + | + | + |
| *Bacillus subtilis* | + | + | + | + | + | + | + | + | + | − | + | + | + | + | + | + | + |
| Candida yeast | + | + | + | + | + | + | + | + | + | + | + | + | + | + | + | + | + |
| Saccharomyces yeast | + | + | + | + | + | + | + | + | + | − | + | + | + | + | + | + | + |
| Aspergillus niger | + | + | + | + | + | + | + | + | + | + | + | + | + | + | + | + | + |
| Gliocladium | + | + | + | + | + | + | + | + | + | − | + | + | + | + | + | + | + |
| Aureobasidium | + | + | + | + | + | + | + | + | + | + | + | + | + | + | + | + | + |
| Cladosporium | + | + | + | + | + | + | + | + | + | − | + | + | + | + | + | + | + |

Notes:
+Inhibition zone was formed.
−Inhibition zone was not formed.

Evaluation Test 2 and Comparative Evaluation Test

Each of Sample Nos. 1, 3, 4, 5, 8, 12, 13, 15, 16, 18, 28, 33 and 34 obtained in Example 1 was added in an amount of 2 g to 100 g of an acrylic resin emulsion coating composition comprising 70% ("%" means "wt%" hereinafter) of emulsion containing 43% of an acrylic resin, 10% of titanium dioxide, 10% of aqueous solution containing 4% of hydroxyethyl cellulose, 8% of 25% aqueous solution of Demol EP (manufactured by Kao Corporation) and 2% of water, and then the composition was stirred. Separately, a coating composition containing no samples was prepared for comparative purpose.

Each of the coating compositions obtained above was coated twice on an aluminum plate of 150 mm in length, 70 mm in width and 2 mm in thickness to form a uniform coating film, which was left to stand for 48 hours at room temperature to obtain specimens. These specimens were immersed in 2 liters of deionized water in a 3 liter glass beaker and were left to stand for 2 weeks in a room exposed to sunlight. Then, these specimens were taken out from the beaker, hydro-extracted and then air-dried.

Furthermore, these specimens were treated using an accelerated weathering test apparatus according to JIS-A1415. After this test, a disc of 20 mm in diameter was cut out from each specimen and was evaluated on antimicrobial activity in the same manner as in Evaluation Test 1. The results are shown in Table 4.

Moreover, the coating compositions containing the microbicides of the present invention were compared with the coating composition containing no microbicide (comparative) and as a result, there were no differences in properties as coating compositions such as discoloration, appearance of coating composition and coating film, drying characteristics and curability.

From these results, it can be seen that the coating composition containing the microbicide of the present invention have excellent antimicrobial activity. Furthermore, concentration of antimicrobial metal ion in deionized water in which the above disc was immersed, was analyzed by atomic absorption spectrometry, and in all cases, it was smaller than limit of detection and presence of the ion could not be recognized.

From the results it can be seen that the microbicide of the present invention and the composition containing it have very low solubility in water and hence can exhibit antimicrobial activity for a prolonged period of time.

were charged at a molar ratio of 1:4:6 and were sufficiently mixed. Thereafter, the mixture was fired at 1300° C. to obtain a compound having the formula of $LiZr_2(PO_4)_3$.

This compound was ground and then immersed in 2N hydrochloric acid of 80° C. to obtain a compound represented by the following formula: $H_{0.9}Li_{0.1}Zr_2(PO_4)_3$ (hereinafter referred to as "HZP").

Furthermore, the following compounds were prepared in the same manner as above except that titanium oxide or tin oxide was used in place of zirconium oxide.

| | |
|---|---|
| $H_{0.8}Li_{0.2}Ti_2(PO_4)_3$ | (hereinafter referred to as "HTP") |
| $H_{0.9}Li_{0.1}Sn_2(PO_4)_3$ | (hereinafter referred to as "HSP") |

EXAMPLE 2

Each of the above compounds was added to 1/100N aqueous $AgNO_3$ solution, followed by stirring at room temperature for various periods of stirring time. The resulting slurry was filtrated and the residue was washed with pure water until Ag ion was no longer detected in the washing water according to atomic absorption spectrometry.

Composition and wt% of Ag in terms of solid were obtained by analyzing Ag ion concentration in the filtrate and the results are shown in Table 5.

After completion of washing, the residue was wet-ground using water as a medium and subjected to classification using a screen to collect fine particles of 1.0 μm or less. Furthermore, the fine particles were dried at 100° C. overnight to obtain a microbicide comprising the phosphate shown in Table 5.

TABLE 5

| Sample No. | Kind of powder | Solid · liquid ratio (g/ml) | Stirring time (hr) | Composition Ag | H | Li | Weight percent of Ag |
|---|---|---|---|---|---|---|---|
| 35 | HZP | 1/100 | 5 | 0.01 | 0.89 | 0.10 | 0.2 |
| 36 | HZP | 1/300 | 24 | 0.50 | 0.40 | 0.10 | 10.3 |
| 37 | HTP | 1/100 | 7 | 0.02 | 0.78 | 0.20 | 0.5 |
| 38 | HTP | 1/300 | 40 | 0.40 | 0.40 | 0.20 | 10.1 |
| 39 | HSP | 1/100 | 12 | 0.01 | 0.89 | 0.10 | 0.2 |
| 40 | HSP | 1/300 | 48 | 0.40 | 0.50 | 0.10 | 7.6 |

Evaluation Test 3 and Comparative Evaluation Test

The microbicides of Sample Nos. 35–40 obtained in

TABLE 4

| Kind of microorganisms to be tested | Sample No. added to the coating composition | | | | | | | | | | | | | |
|---|---|---|---|---|---|---|---|---|---|---|---|---|---|---|
| | 1 | 3 | 4 | 5 | 8 | 12 | 13 | 15 | 16 | 18 | 28 | 33 | 34 | None |
| *Escherichia coli* | + | + | + | + | + | + | + | + | + | + | + | + | + | − |
| *Pseudomonas aeruginosa* | + | + | + | + | + | + | + | + | + | + | + | + | + | − |
| *Staphylococcus aureus* | + | + | + | + | + | + | + | + | − | + | + | + | + | − |
| *Bacillus subtilis* | + | + | + | + | + | + | + | + | + | + | + | + | + | − |
| Candida yeast | + | + | + | + | + | + | + | + | + | + | + | + | + | − |
| Saccharomyces yeast | + | + | + | + | + | + | + | + | + | + | + | + | + | − |
| Aspergillus niger | + | + | + | + | + | + | + | − | + | + | + | + | + | − |
| Gliocladium | + | + | + | − | + | + | + | + | + | + | + | + | + | − |
| Aureobasidium | + | + | + | + | + | + | + | + | + | + | + | + | + | − |
| Cladosporium | + | + | + | + | + | + | + | + | + | + | + | + | + | − |

Notes:
+ Inhibition zone was formed.
− Inhibition zone was not formed.

REFERENTIAL EXAMPLE 4

Lithium carbonate ($Li_2CO_3$), zirconium oxide ($ZrO_2$) and ammonium dihydrogenphosphate ($NH_4H_2PO_4$)

Example 2 were evaluated on antimicrobial activity in the same manner as in Evaluation Test 1. Furthermore, molded products made in the same manner using HZP, HTP and HSP which were obtained in Referential Example 4 and on which Ag was not supported (Sample No. P1, Sample No. P2 and Sample No. P3, respectively), and molded products made without adding HZP, HTP and HSP were also evaluated similarly on antimicrobial activity (for comparative purpose). The results are shown in Table 6. From Table 6, it can be seen that the molded products containing the microbicide of the present invention have excellent antimicrobial activity.

TABLE 6

| Sample No. | Results of evaluation | | | | | | | | |
|---|---|---|---|---|---|---|---|---|---|
| | 35 | 36 | 37 | 38 | 39 | 40 | P1 | P2 P3 | None |
| Kind of tested microorganisms | | | | | | | | | |
| *Escherichia coli* | + | + | + | + | + | + | − | − − | − |
| *Pseudomonas aeruginosa* | + | + | + | + | + | + | − | − − | − |
| *Staphylococcus aureus* | + | + | + | + | + | + | − | − − | − |
| *Bacillus subtilis* | + | + | + | + | + | + | − | − − | − |
| Candida yeast | + | + | + | + | + | + | − | − − | − |
| Saccharmoyces yeast | + | + | + | + | + | + | − | − − | − |
| Aspergillus niger | + | + | + | + | + | + | − | − − | − |
| Gliocladium | + | + | + | + | + | + | − | − − | − |
| Aureobasidium | + | + | + | + | + | + | − | − − | − |
| Cladosporium | + | + | + | + | + | + | − | − − | − |

Notes:
+Inhibition zone was formed.
−Inhibition zone was not formed.

Evaluation Test 4 and Comparative Evaluation Test

The microbicides of Sample Nos. 35–40 obtained in Example 2 were evaluated on antimicrobial activity in the same manner as in Evaluation Test 2 except that immersion treatment with deionized water was not carried out and addition amount of the microbicide was as shown in Table 7. Furthermore, the same evaluation was conducted on the sample containing no microbicide (comparative). The results are shown in Table 8.

There were no differences between the coating composition containing the microbicide of the present invention and the coating composition containing no microbicide (comparative) in properties as coating compositions such as discoloration, appearance of coating composition and coating film, drying characteristics and curability.

Thus, it can be seen that the coating compositions containing the microbicides of the present invention have excellent antimicrobial activity.

TABLE 7

| Sample No. | Addition amount (g) of microbicide per 100 g of coating composition |
|---|---|
| 35 | 2.0 |
| 36 | 0.1 |
| 37 | 1.0 |
| 38 | 0.2 |
| 39 | 2.0 |
| 40 | 0.2 |

TABLE 8

| Sample No. | Results of evaluation | | | | | | |
|---|---|---|---|---|---|---|---|
| | 35 | 36 | 37 | 38 | 39 | 40 | None |
| Kind of tested microorganisms | | | | | | | |
| *Escherichia coli* | + | + | + | + | + | + | − |
| *Pseudomonas aeruginosa* | + | + | + | + | + | + | − |
| *Staphylococcus aureus* | + | + | + | + | + | + | − |
| *Bacillus subtilis* | + | + | + | + | + | + | − |
| Candida yeast | + | + | + | + | + | + | − |
| Saccharomyces yeast | + | + | + | + | + | + | − |

TABLE 8-continued

| Sample No. | Results of evaluation | | | | | | |
|---|---|---|---|---|---|---|---|
| | 35 | 36 | 37 | 38 | 39 | 40 | None |
| Aspergillus niger | + | + | + | + | + | + | − |
| Gliocladium | + | + | + | + | + | + | − |
| Aureobasidium | + | + | + | + | + | + | − |
| Cladosporium | + | + | + | + | + | + | − |

Evaluation Test 5

Specimens prepared in Evaluation Test 4 were treated according to JIS-A1415 using an accelerated weathering test apparatus for 500 hours. Then, a disc of 20 mm in diameter was cut out from each specimen and was evaluated on antimicrobial activity in the same manner as in Evaluation Test 1. The results were the same as those obtained in Evaluation Test 4.

From the results, it can be seen that the antimicrobial compositions containing the microbicides of the present invention exhibit antimicrobial activity for a very long period of time.

Evaluation Test 6

Each of the microbicides of Sample Nos. 35–40 prepared in Example 2 was added at a concentration of 2% to nylon 6 dry chips having an intrinsic viscosity [$\eta$] of 2.3 measured in 95% sulfuric acid and mixed therewith. The mixture was melt-spun and then stretched in the uusual manner to obtain six kinds of stretched yarns of 120 deniers/4 filaments.

These stretched yarns were knitted into a tube and scoured. Then, a specimen of 20 mm in diameter was cut out therefrom, and antimicrobial activity thereof was evaluated in the same manner as in Evaluation Test 3. As a result, inhibition zones were formed in all cases as shown in Table 9.

TABLE 9

| Sample No. | Results of evaluation | | | | | |
|---|---|---|---|---|---|---|
| | 35 | 36 | 37 | 38 | 39 | 40 |
| Kind of tested microorganisms | | | | | | |
| *Escherichia coli* | + | + | + | + | + | + |
| *Pseudomonas aeruginosa* | + | + | + | + | + | + |
| *Staphylococcus aureus* | + | + | + | + | + | + |
| *Bacillus subtilis* | + | + | + | + | + | + |
| Candida yeast | + | + | + | + | + | + |
| Saccharmoyces yeast | + | + | + | + | + | + |
| Aspergillus niger | + | + | + | + | + | + |
| Gliocladium | + | + | + | + | + | + |
| Aureobasidium | + | + | + | + | + | + |
| Cladosporium | + | + | + | + | + | + |

Evaluation Test 7 and Comparative Evaluation Test

The stretched yarns obtained in Evaluation Test 6 were knitted into a tube and this was scoured to obtain a tube-knitted cloth.

For comparison, three kinds of powders of silver particles, silver-carrying active carbon and silver-type zeolite which was obtained by adding 500 ml of 1/10M aqueous silver nitrate solution to 250 g of A-type zeolite ($0.94Na_2O.Al_2O_3.1.92SiO_2.xH_2O$/average particle size 1.1 μm) and stirring the mixture at room temperature for 3 hours, were ground and classified to obtain fine powders of 1.0 μm, 1.1 μm and 1.1 μm in their average particle sizes. In the same manner, tubeknitted clothes were produced using these fine powders (comparative).

The clothes thus obtained were left to stand for 2 years in the outdoors under no direct sunshine and poor ventilation and the state was observed. The results are shown in Table 10.

Furthermore, the tube-knitted clothes were washed according to JIS-0217 (method 105) repeatedly 100 times and then, specimens were cut out therefrom and antimicrobial activity thereof was evaluated in the same manner as in Evaluation Test 1. As a result, inhibition zone was formed in the clothes containing the microbicide of the present invention, while no inhibition zone was formed in the comparative clothes.

From the above results, it can be seen that the molded products containing the microbicide of the present invention retain antimicrobial activity for a very long period of time.

TABLE 10

| Sample No. or kind of powders | State of tube-knitted cloth |
| --- | --- |
| 35 | No change |
| 36 | No change |
| 37 | No change |
| 38 | No change |
| 39 | No change |
| 40 | No change |
| Silver particles | Fungi grew much. |
| Silver-carrying active carbon | Fungi grew much. |
| Silver type zeolite | Some fungi grew. |

REFERENTIAL EXAMPLE 5

The compound having the formula $LiZr_2(PO_4)_3$ obtained in Referential Example 4 was ground and then added to an aqueous solution of nitrate of sodium or potassium and subjected to stirring, washing with water, drying and grinding to obtain a phosphate of $NaZr_2(PO_4)_3$ or $KZr_2(PO_4)_3$.

Furthermore, a phosphate of $LiTi_2(PO_4)_3$ was obtained in the same manner as above except that titanium oxide was used in place of zirconium oxide.

REFERENTIAL EXAMPLE 6

The zirconium phosphate obtained in Referential Example 1 was added to an aqueous solution of nitrate of sodium or potassium and subjected to stirring, washing with water, drying and grinding to obtain a phosphate of $Na_2Zr(PO_4)_2$ or $K_2Zr(PO_4)_2$.

EXAMPLE 3

Microbicides were prepared by the following method using powders of the phosphates obtained in Referential Examples 5-6.

That is, the powders obtained in Referential Examples 5-6 were added to aqueous solutions containing nitrates of antimicrobial metals at various concentrations, followed by stirring for 15 hours. Thereafter, the resulting slurries were subjected to filtration and sufficient washing with pure water. Further, these were dried by heating at 110° C. overnight to obtain the desired microbicides of the present invention.

Separately, A-type zeolite (composition: $0.94Na_2O.Al_2O_3.1.92SiO_2.xH_2O$) was added to an aqueous solution of silver nitrate alone or of silver nitrate and ammonium nitrate, followed by stirring at room temperature for 5 hours, then sufficient washing with water and drying at 110° C. to obtain antimicrobial zeolites (comparative examples).

The resulting microbicides are shown in Table 11.

TABLE 11

| Sample No. | Microbicide |
| --- | --- |
| 41 | $Ag_{0.01}Li_{0.99}Zr_2(PO_4)_3$ |
| 42 | $Ag_{0.05}Na_{0.95}Zr_2(PO_4)_3$ |
| 43 | $Ag_{0.1}(NH_4)_{0.9}Ti_2(PO_4)_3$ |
| 44 | $Cu_{0.15}K_{0.7}Zr_2(PO_4)_3$ |
| 45 | $Ag_{0.07}Na_{1.93}Zr(PO_4)_2$ |
| 46 | $Fe_{0.05}K_{1.9}Zr(PO_4)_2$ |
| 47 | $0.03Ag_2O.0.8Na_2O.Al_2O_3.1.99SiO_2.XH_2O$ |
| 48 | $0.03Ag_2O.0.02(NH_4)_2O.0.8Na_2O.Al_2O_3.1.9SiO_2.XH_2O$ |
| 49 | $LiZr_2(PO_4)_3$ |

Sample Nos. 47, 48 and 49 are comparative samples.

Evaluation Test 8 and Comparative Evaluation Test

Antimicrobrial activity of the microbicides obtained in Example 3 was evaluated by measuring minimum inhibitory concentration (MIC) for bacteria, yeast and fungus.

As microorganisms to be tested, the following ones were used. That is, *Escherichia coli* and *Pseudomonas aeruginosa* were used as bacteria, *Candida yeast* was used as a yeast, and *Aspergillus niger* was used as a fungus.

As a growth medium, Muller-Hinton medium was used for the bacteria, potato dextrose agar medium was used for the fungus, and Yeast Morphology Agar was used for the yeast.

As a sensitivity-measuring medium, Muller-Hinton medium was used for the bacteria and Sabouraud's agar medium was used for the fungus and yeast.

A sensitivity-measuring plate was prepared in the following manner.

A dilution stage suspension of each sample was prepared with sterilized and purified water. This was dissolved and added to the sensitivity-measuring medium of 50-60° C. in an amount of 1/9 that of the medium. The resulting medium was well mixed, and the mixture was dividedly poured in petri dishes and solidified to obtain a sensitivity-measuring plate.

Preparation of inoculation bacteria solution was carried out by inoculating the subcultured strain to be tested in the growth medium, culturing the strain and then diluting it with the growth medium so that the number of bacteria was $10^6$/ml. Inoculation solution for testing of fungi was prepared by inoculating the subcultured strain to be tested in the growth medium, culturing it, and then floating the resulting medium in 0.05% Poly-solvate 80 sterilized solution so that the number of fungi reached about $10^6$/ml. Inoculation solution for yeast was prepared by inoculating the subcultured strain to be tested in the growth medium, culturing it and then, floating the produced medium in sterilized physiological saline solution so that the number of yeasts was about $10^6$/ml.

Test for minimum inhibitory concentration was conducted as follows: The inoculation solution was streak-coated in about 2 cm on the sensitivity-measuring plate by a Nichrome wire loop (inner diameter about 1 mm) and culturing was carried out for 18-20 hours at 37° C. for bacteria and for 7 days at 25° C. for fungi. After culturing for the given period, the minimum concentration at which growth was inhibited, was adopted as minimum inhibitory concentration.

The results are shown in Table 12.

TABLE 12

| Sample No. | Minimum inhibitory concentration (ppm) | | | |
|---|---|---|---|---|
| | Escherichia coli | Pseudomonas aeruginosa | Candida yeast | Aspergillus niger |
| 41 | 125 | 125 | 500 | 500 |
| 42 | 62.5 | 125 | 500 | 500 |
| 43 | 62.5 | 62.5 | 250 | 500 |
| 44 | 1000 | 2000 | >2000 | 1000 |
| 45 | 125 | 62.5 | 500 | 250 |
| 46 | >2000 | 2000 | >2000 | >2000 |
| 47 | 125 | 125 | 500 | 1000 |
| 48 | 62.5 | 62.5 | 500 | 500 |
| 49 | >2000 | >2000 | >2000 | >2000 |

Evaluation Test 9 and Comparative Evaluation Test

To the microbicides obtained in Example 3 were added 3 wt% of sepiolite as a binder and 3 wt% of titanium oxide or ascorbic acid as a discoloration accelerating material, followed by well mixing of them. Then, tablets of 13 mm in diameter and 5 mm in height were molded from the mixture by a tabletting machine under a pressure of 200 kg/cm$^2$.

Color of the tablets just after molded and that of the tablets exposed to sunlight for 3 days indoors were measured by color-difference meter SZ-Σ80 manufactured by Nihon Denshoku Kogyo Co., Ltd., and color difference was obtained by comparing the color with color of a tablet of Sample No. 49 which contained no antimicrobial metal just after molded. The results are shown in Table 13.

TABLE 13

| | Color difference (ΔE) | | | |
|---|---|---|---|---|
| | Titanium oxide type | | Ascorbic acid type | |
| Sample No. | Just after molded | After exposure | Just after molded | After exposure |
| 41 | 2 | 1 | 0.3 | 0.9 |
| 42 | 1 | 1 | 1 | 2 |
| 43 | 1 | 2 | 2 | 3 |
| 44 | 2 | 2 | 4 | 6 |
| 45 | 3 | 27 | 18 | 29 |
| 46 | 1 | 4 | 5 | 7 |
| 47 | 2 | 21 | 6 | 22 |
| 48 | 2 | 12 | 2 | 18 |
| 49 | 0 | — | 0 | 0.8 |

Evaluation Test 10

Each of the various microbicides obtained in Example 3 was added to 4% aqueous acetic acid solution (pH=3) in an amount of 10%, and the solution was left to stand for 4 hours. Then, the microbicide was filtrated off and elution amount of the antimicrobial metal in the filtrate was measured by an atomic absorption photometer. The results are shown in Table 14.

TABLE 14

| Sample No. | Antimicrobial metal | Elution amount (ppm) |
|---|---|---|
| 41 | Ag | 0.1 or less |
| 42 | Ag | 0.1 or less |
| 43 | Ag | 0.1 or less |
| 44 | Cu | 0.1 or less |
| 45 | Ag | 0.1 or less |
| 46 | Fe | 0.1 or less |
| 47 | Ag | 5 |
| 48 | Ag | 4 |

Evaluation Test 11 and Comparative Evaluation Test

Each of the microbicides obtained in Example 3 was added in an amount of 10% to an acrylic coating composition (10% in solid content), followed by sufficient stirring to prepare an antimicrobial coating composition.

This coating composition was coated on a polyester paper at a coating amount of the microbicide of 0.1 g/m$^2$ to prepare an antimicrobial coated paper.

The coated paper was immersed in an aqueous nitric acid solution of pH 2 overnight and thereafter was well washed with water and was evaluated on antimicrobial activity.

Evaluation of antimicrobial activity was conducted in the following manner.

Escherichia coli was used as bacterial to be used. The bacteria solution was inoculated on the coated paper so that the number of bacteria was $10^4$–$10^5$ per 25 cm$^2$ and this was stored at 37° C. Just after starting of storage (just after inoculation) and after lapse of 24 hours, the bacteria in the coated paper were washed away with a bacteria number-measuring medium (SCDLP liquid medium), and the washing liquid was used as a test solution. The number of surviving bacteria in this test solution was measured by plate culturing method (at 37° C. for 2 days) with the bacteria number-measuring medium, and this was shown in terms of the number of living bacteria per 25 cm$^2$ of the coated paper. The results are shown in Table 15.

TABLE 15

| Sample No. | Just after starting of storing | After lapse of 24 hours |
|---|---|---|
| 41 | 6.3 × 10$^5$ | 10 or less |
| 42 | 6.2 × 10$^5$ | 10 or less |
| 43 | 8.2 × 10$^5$ | 10 or less |
| 44 | 3.9 × 10$^5$ | 2.0 × 10$^2$ |
| 45 | 3.0 × 10$^5$ | 10 or less |
| 46 | 1.0 × 10$^5$ | 3.8 × 10$^4$ |
| 47 | 2.4 × 10$^5$ | 7.6 × 10$^3$ |
| 48 | 1.7 × 10$^5$ | 9.1 × 10$^2$ |
| 49 | 6.0 × 10$^4$ | 7.2 × 10$^5$ |

As clear from the above results of evaluation tests, the microbicides of the present invention are chemically and physically stable and are very useful as materials which can exhibit antimicrobial activity for a prolonged period of time even under severe conditions.

What is claimed is:

1. A microbicide phosphate represented by the following general formula:

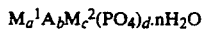

$$M^1_a A_b M^2_c (PO_4)_d \cdot nH_2O$$

wherein $M^1$ is silver $M^2$ is zirconium or titanium,

A represents at least one ion selected from the group consisting of hydrogen ion, alkali metal ions, and ammonium ion, n represents a number which satisfies $0 \leq n \leq 6$, a and b each represents a positive number and satisfies the equation $la + mb = 1$, where l is valence of $M^1$ and m is valence of A, and c is 2 and d is 3.

2. A microbicide according to claim 1, wherein A is lithium, sodium or potassium ion.

3. A microbicide according to claim 1, wherein $a = 0.01 + 0.5$.

4. A microbicide according to claim 1, wherein A is hydrogen ion or ammonium ion.

5. A microbicide according to claim 1 wherein the formula is $Ag_{0.01}Li_{0.99}Zr_2(PO_4)_3$.

6. A method of inhibiting the growth of microorganisms on a surface comprising coating or impregnating said surface with an antimicrobially effective amount of the microbicide of claim 1.

7. A method of inhibiting the growth of microorganisms in a liquid comprising contacting said liquid with an antimicrobially effective amount of the microbicide of claim 1.

8. A method of inhibiting the growth of microorganisms in a solid comprising coating or impregnating said solid with an antimicrobially effective amount of the microbicide of claim 1.

* * * * *